(12) United States Patent
Iwano et al.

(10) Patent No.: US 12,023,456 B2
(45) Date of Patent: *Jul. 2, 2024

(54) BALLOON CATHETER

(71) Applicant: GOODMAN CO., LTD., Nagoya (JP)

(72) Inventors: Kenshi Iwano, Seto (JP); Takamasa Miyake, Seto (JP); Tomokazu Ogawa, Seto (JP); Keisuke Ogawa, Seto (JP); Soichiro Fujisawa, Seto (JP); Mitsuhiro Ota, Seto (JP)

(73) Assignee: GOODMAN CO., LTD., Nagoya (JP)

( * ) Notice: Subject to any disclaimer, the term of this patent is extended or adjusted under 35 U.S.C. 154(b) by 562 days.

This patent is subject to a terminal disclaimer.

(21) Appl. No.: 17/071,230

(22) Filed: Oct. 15, 2020

(65) Prior Publication Data

US 2021/0023347 A1    Jan. 28, 2021

Related U.S. Application Data

(63) Continuation of application No. 15/499,996, filed on Apr. 28, 2017, now Pat. No. 10,842,971, which is a
(Continued)

(30) Foreign Application Priority Data

Oct. 30, 2014   (JP) .................................. 2014-221134

(51) Int. Cl.
*A61M 25/00*   (2006.01)
*A61M 25/01*   (2006.01)
(Continued)

(52) U.S. Cl.
CPC ............ *A61M 25/10* (2013.01); *A61M 25/00* (2013.01); *A61M 25/01* (2013.01); *A61M 25/09* (2013.01);
(Continued)

(58) Field of Classification Search
CPC .. A61M 2025/1068; A61M 2025/1084; A61M 2025/1086; A61M 25/00; A61M 25/01; A61M 25/09; A61M 25/10
See application file for complete search history.

(56) References Cited

U.S. PATENT DOCUMENTS 4,723,936 A    2/1988  Buchbinder et al.
4,848,344 A    7/1989  Sos et al.
(Continued)

FOREIGN PATENT DOCUMENTS

EP    0254701 A1    1/1988
EP    0344530 A1    12/1989
(Continued)

OTHER PUBLICATIONS

Mar. 11, 2021—EP Office Communication—App (EP) 15855569.8.
(Continued)

*Primary Examiner* — William R Carpenter
(74) *Attorney, Agent, or Firm* — Banner & Witcoff, Ltd.

(57) ABSTRACT

A balloon catheter includes an outer shaft, an inner shaft, and an inflatable balloon. The inner shaft is inserted inside the outer shaft. A part of the inner shaft extends from a leading end of the outer shaft. The balloon includes a base end side joint portion joined to the outer shaft and a leading end side joint portion joined to the inner shaft. The inner shaft has an extension portion configured to in an axial line direction. The extension portion is provided further to a base end side than the leading end side joint portion.

13 Claims, 4 Drawing Sheets

Related U.S. Application Data continuation-in-part of application No. PCT/JP2015/080334, filed on Oct. 28, 2015.

(51) Int. Cl.
*A61M 25/09* (2006.01)
*A61M 25/10* (2013.01)

(52) U.S. Cl.
CPC ............ *A61M 2025/1068* (2013.01); *A61M 2025/1084* (2013.01); *A61M 2025/1086* (2013.01)

(56) References Cited

U.S. PATENT DOCUMENTS

| | | | | |
|---|---|---|---|---|
| 5,032,113 | A | * | 7/1991 | Burns ................. A61M 25/104 604/523 |
| 5,383,853 | A | * | 1/1995 | Jung ................. A61M 25/0068 606/194 |
| 5,830,227 | A | | 11/1998 | Fischell et al. |
| 6,036,670 | A | | 3/2000 | Wijeratne et al. |
| 8,100,855 | B2 | * | 1/2012 | Consigny ............. A61M 25/10 604/93.01 |
| 2002/0007146 | A1 | | 1/2002 | Omaleki et al. |
| 2003/0060802 | A1 | | 3/2003 | Omaleki et al. |
| 2003/0105426 | A1 | * | 6/2003 | Jorgensen ......... A61M 25/1006 604/103.1 |
| 2006/0287665 | A1 | | 12/2006 | Burton et al. |
| 2009/0036829 | A1 | * | 2/2009 | Pagel ................. A61M 25/104 604/96.01 |
| 2009/0171278 | A1 | | 7/2009 | Hirszowicz et al. |
| 2012/0143130 | A1 | | 6/2012 | Subramaniam et al. |
| 2012/0197193 | A1 | | 8/2012 | Krolik et al. |
| 2012/0316585 | A1 | * | 12/2012 | Jeffrey ................ A61M 25/005 606/159 |
| 2013/0300241 | A1 | | 11/2013 | Wedman et al. |

FOREIGN PATENT DOCUMENTS

| | | | |
|---|---|---|---|
| EP | 0829269 | A1 | 3/1998 |
| EP | 0875263 | A2 | 11/1998 |
| JP | S63-46172 | A | 2/1988 |
| JP | H02-063474 | A | 3/1990 |
| JP | H10-085339 | A | 4/1998 |
| JP | H10-305102 | A | 11/1998 |
| JP | 2003-520060 | A | 7/2003 |
| JP | 2008-237844 | A | 10/2008 |
| JP | 2009511149 | A | 3/2009 |
| JP | 2009-112361 | A | 5/2009 |
| JP | 5002417 | B2 | 8/2012 |
| JP | 2015520596 | A | 7/2015 |
| WO | 00-50113 | A2 | 8/2000 |
| WO | 2006127920 | A1 | 11/2006 |
| WO | 2007054364 | A2 | 5/2007 |
| WO | 2013-134704 | A1 | 9/2013 |
| WO | 2016-068167 | A1 | 5/2016 |

OTHER PUBLICATIONS

Jan. 26, 2016—International Search Report—Intl App PCT/JP2015/080334.
Dec. 12, 2017—(JP) Office Action—App 2014-221134—Eng Tran.
May 2, 2017—English Translation of International Preliminary Report On Patentability—Intl App PCT/JP2015/080334.
Jul. 31, 2018—(JP) Office Action—App 2014-221134—Eng Tran.
Jun. 28, 2018—Extended European Search Report—App (EP) 15855569.8.
Apr. 2, 2019 (CN) Office Action—App 201580054353.2—Eng Tran.
Jan. 30, 2019—(US) Non-Final Office Action—U.S. Appl. No. 15/499,996.
May 17, 2019—(US) Final Office Action—U.S. Appl. No. 15/499,996.
Oct. 31, 2019 (CN) Office Action—App 201580054353.2—Eng Tran.
Feb. 25, 2020—(US) Non-final Office Action—U.S. Appl. No. 15/499,996.
Jul. 16, 2020—(US) Non-final Office Action—U.S. Appl. No. 15/499,996.
Aug. 22, 2023—EP App 15855569.8 Office Communication.

* cited by examiner

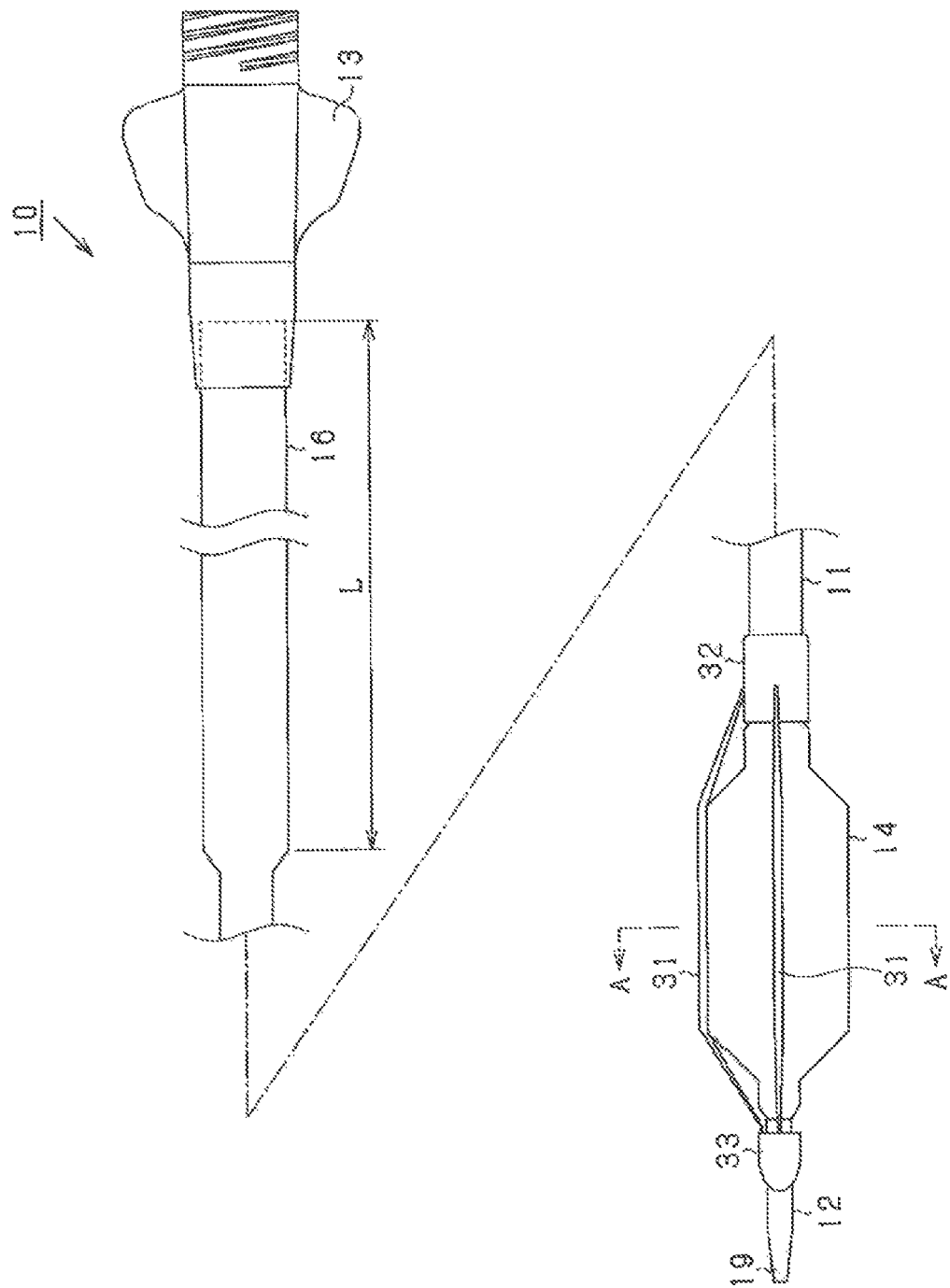

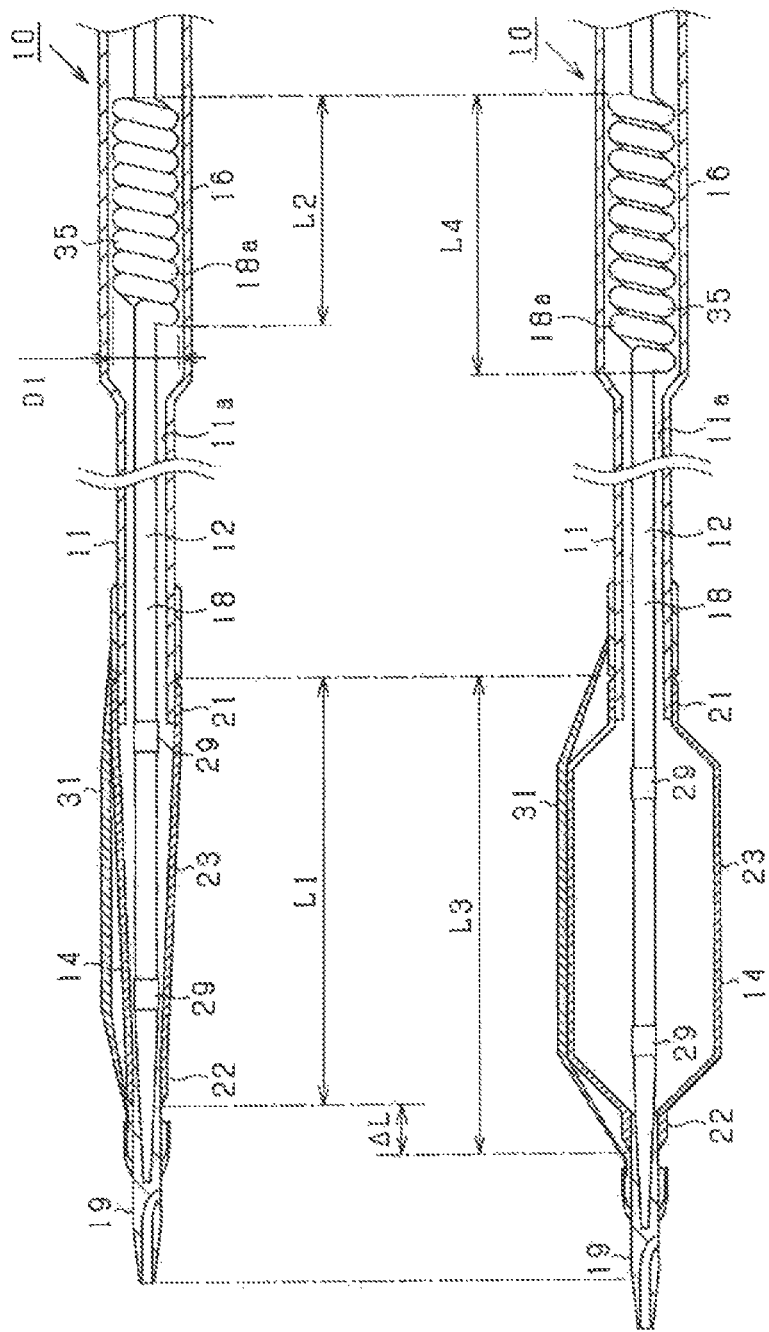

BALLOON CATHETER

CROSS-REFERENCE TO RELATED APPLICATION

This application is a continuation of U.S. Non-Provisional patent application Ser. No. 15/499,996, filed Apr. 28, 2017, which is a continuation-in-part of International Application No. PCT/JP2015/080334, filed Oct. 28, 2015, which claims priority from Japanese Patent Application No. 2014-221134, filed on Oct. 30, 2014. The disclosure of the foregoing applications are hereby incorporated by reference in their entirety.

BACKGROUND

The present disclosure relates to a balloon catheter.

In treatments such as PTA (percutaneous transluminal angioplasty) and PTCA (percutaneous transluminal coronary angioplasty), a balloon catheter is used. The balloon catheter is provided with a catheter shaft and a balloon. The balloon is provided on a distal end side of the catheter shaft. A user of the balloon catheter introduces the balloon into a constricted section or a blocked section that has occurred in a blood vessel, and dilates (inflates) the balloon, thus treating the constricted or blocked section.

The catheter shaft is provided with an outer shaft and an inner shaft. The inner shaft is inserted inside the outer shaft. A base end portion of the balloon is joined to a leading end portion of the outer shaft. The balloon catheter is configured such that the balloon inflates or deflates as a result of a compressed fluid flowing through a lumen of the outer shaft.

A leading end portion of the inner shaft extends further to the leading end side than a leading end of the outer shaft. The portion of the inner shaft that extends from the leading end of the outer shaft is covered by the balloon. The leading end portion of the inner shaft is joined to a leading end portion of the balloon. A base end portion of the inner shaft is joined to a partway position or the like of the outer shaft.

SUMMARY

When the balloon inflates, it is conceivable that an extending (expanding) force acts not only in a radial direction but also in an axial line direction. As described above, the base end portion of the balloon is joined to the outer shaft. Thus, when the force that extends in the axial line direction acts on the balloon, the balloon tries to extend toward the leading end side with respect to the outer shaft. Meanwhile, the leading end portion of the balloon is joined to the inner shaft. Then, the base end portion of the inner shaft is joined to the outer shaft and so on. As a result, even when the balloon tries to extend toward the leading end side, displacement of the leading end portion of the balloon toward the leading end side is restricted by the inner shaft. It is therefore supposed that, in accordance with the inflation of the balloon, the balloon becomes warped into a banana shape. In this case, it is feared that a problem such as damage to the blood vessel may occur due to the warping of the balloon.

Various embodiments of the broad principles derived herein provide a balloon catheter capable of suppressing warping of a balloon.

Embodiments provide a balloon catheter that includes an outer shaft, an inner shaft, and an inflatable balloon. The inner shaft is inserted inside the outer shaft. A part of the inner shaft extends from a leading end of the outer shaft. The balloon includes a base end side joint portion joined to the outer shaft and a leading end side joint portion joined to the inner shaft. The inner shaft has an extension portion configured to extend in an axial line direction. The extension portion is provided further to a base end side than the leading end side joint portion.

BRIEF DESCRIPTION OF THE DRAWINGS

Embodiments will be described below in detail with reference to the accompanying drawings in which:

FIG. 1 is an overall side view showing a configuration of a balloon catheter;

FIG. 3A and FIG. 3B are vertical cross sections illustrating operations of a coil portion, where FIG. 3A shows a deflated state of a balloon and FIG. 3B shows an inflated state of the balloon.

DETAILED DESCRIPTION

Figure 2A:
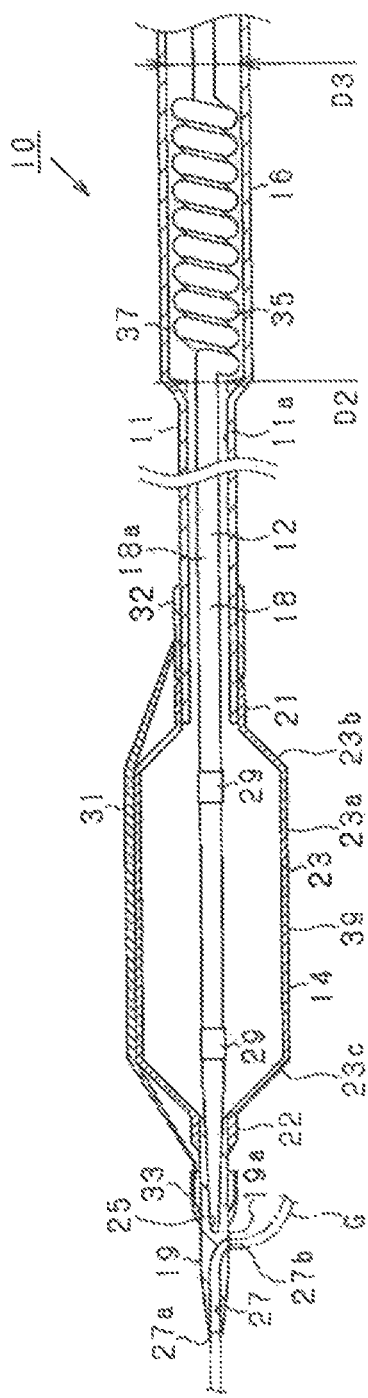
FIG. 2A is a vertical cross section showing the configuration of the balloon catheter.
Figure 2B:
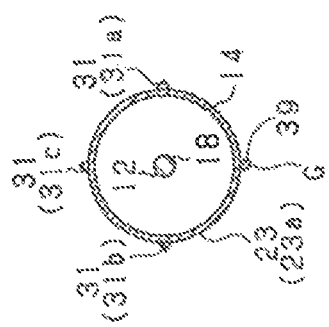
FIG. 2B is a cross-sectional view along a line A-A shown in FIG. 1.

Hereinafter, an embodiment will be explained with reference to the drawings. FIG. 1 is an overall side view showing a configuration of a balloon catheter. FIG. 2A is a vertical cross section showing the configuration of the balloon catheter, and FIG. 2B is a cross-sectional view along a line A-A shown in FIG. 1. Note that in FIG. 2A and FIG. 2B, a balloon is shown in an inflated state.

As shown in FIG. 1 and FIG. 2A, a balloon catheter 10 is provided with an outer shaft 11, an inner shaft 12, and a balloon 14. The inner shaft 12 is inserted inside the outer shaft 11. Further, a hub 13 is attached to a base end portion (a proximal portion) of the outer shaft 11 and the inner shaft 12. The balloon 14 is attached to a leading end side (a distal end side) of the outer shaft 11 and the inner shaft 12.

The outer shaft 11 is a flexible tubular member. The outer shaft 11 is formed of a resin material, and is, for example, formed of a polyamide elastomer. A lumen 11a is formed in the outer shaft 11 and extends along the whole area of the outer shaft 11 in the axial line direction. The lumen 11a is a through hole that extends in the axial line direction of the outer shaft 11. The lumen 11a communicates with the interior of the balloon 14 and also communicates with the interior of the hub 13.

The outer shaft 11 includes an expanded diameter portion 16. The expanded diameter portion 16 is a portion whose inner diameter and outer diameter are larger than the inner diameter and outer diameter of a portion further to the leading end side than the expanded diameter portion 16. The expanded diameter portion 16 is formed in the outer shaft 11 over a predetermined range that includes the base end portion of the outer shaft 11. Specifically, the expanded diameter portion 16 is formed over a range from the base end portion of the outer shaft 11 to a position on the leading end side separated from the base end portion by a predetermined dimension L. The predetermined dimension L is 5 mm to 300 mm, for example. Specifically, in the present embodiment, the outer shaft 11 includes a small diameter portion and the expanded diameter portion 16. The leading end portion of the expanded diameter portion 16 is a tapered portion whose outer diameter and inner diameter become gradually smaller toward the leading end side. The small diameter portion is a section that extends to the leading end side from a leading end of the expanded diameter portion 16.

Specifically, the small diameter portion extends toward the leading end side from the leading end of the tapered portion of the expanded diameter portion 16. The inner diameter and the outer diameter of the small diameter portion are constant in the axial line direction. The inner diameter and the outer diameter of the expanded diameter portion 16 are, respectively, larger than the inner diameter and the outer diameter of the small diameter portion. Note that the leading end portion of the expanded diameter portion 16 need not necessarily be the tapered portion. The leading end portion of the expanded diameter portion 16 may be, for example, a curved portion whose diameter becomes smaller toward the leading end side.

It should be noted that the outer shaft 11 need not necessarily be formed of the same material across the whole area in the axial line direction. For example, the outer shaft 11 may be formed by a plurality of tubes formed from different materials being connected in the axial line direction. In this case, of the plurality of tubes configuring the outer shaft 11, it is conceivable that a tube positioned on the base end side be formed of a metal material having a relatively high rigidity, and a tube positioned on the leading end side be formed of the resin material (the polyamide elastomer) having a relatively low rigidity.

The inner shaft 12 has a core wire 18 and a leading end tip 19. The leading end tip 19 is joined to the leading end side of the core wire 18. The core wire 18 is formed of a metal wire. The core wire 18 is, for example, formed of a stainless steel wire. A wire 18a that configures the core wire 18 has a circular shape in a transverse cross section. The transverse cross section is a cross section perpendicular to the axial line direction of the core wire 18. A leading end portion of the core wire 18 is tapered toward the leading end. Apart from the leading end portion, the outer diameter of the core wire 18 is substantially constant along the whole area in the axial line direction. The outer diameter of the core wire 18 (the wire 18a) is smaller than the inner diameter of the outer shaft 11. More specifically, the outer diameter of the core wire 18 is smaller than the inner diameter of the section to the leading end side of the expanded diameter portion 16 in the outer shaft 11. Thus, a predetermined gap is formed between an outer peripheral surface of the core wire 18 and in inner peripheral surface of the outer shaft 11. Further, the base end portion of the core wire 18 is fixed to the hub 13.

Note that the core wire 18 may be formed of a material other than the stainless steel. The core wire 18 may be formed, for example, of a superelastic alloy, such as a nickel titanium alloy or the like. Further, the core wire 18 may be formed such that the outer diameter becomes smaller, in a stepped manner or in a continuous manner, from the base end side toward the leading end side.

The leading end tip 19 is formed of a pliable resin material. A hole portion 25 that is open toward the base end side is formed in the leading end tip 19. The leading end portion of the core wire 18 is inserted into the hole portion 25. In a state in which the leading end portion of the core wire 18 is inserted into the hole portion 25, the leading end tip 19 and the core wire 18 are joined together and integrated.

A part of the inner shaft 12 extends further to the leading end side than the leading end of the outer shaft 11. The balloon 14 is provided such that it covers, from the outside, the area of the inner shaft 12 extending from the leading end of the outer shaft 11. The balloon 14 is formed of a thermoplastic polyamide elastomer. However, the balloon 14 may be formed of another thermoplastic resin, such as polyethylene, polypropylene, or the like.

The balloon 14 has a base end side joint portion 21, a leading end side joint portion 22, and an inflation portion 23. The base end side joint portion 21 is a base end side portion of the balloon 14, and is the portion that is joined to the leading end portion of the outer shaft 11. The leading end side joint portion 22 is a leading end side portion of the balloon 14 and is the portion that is joined to the leading end portion of the inner shaft 12. The base end side joint portion 21 and the leading end side joint portion 22 are, respectively, cylindrical portions that extend from the inflation portion 23. The leading end portion of the outer shaft 11 is inserted into the base end side joint portion 21. In a state in which the leading end portion of the outer shaft 11 is inserted into the base end side joint portion 21, the base end side joint portion 21 and the outer shaft 11 are joined together. Further, the inner shaft 12 is inserted into the leading end side joint portion 22. Specifically, the leading end side joint portion 22 is disposed such that it covers a joint portion between the core wire 18 and the leading end tip 19 in the inner shaft 12. In the present embodiment, the leading end side joint portion 22, the leading end tip 19, and the core wire 18 are overlapped with each other in the radial direction. In this state, the leading end side joint portion 22, the leading end tip 19, and the core wire 18 are joined together by thermal welding. In addition, in this joined state, a base end portion of the leading end tip 19 is substantially in the same position as the base end portion of the leading end side joint portion 22.

The inflation portion 23 is positioned between the base end side joint portion 21 and the leading end side joint portion 22, and is configured to inflate or deflate. The inflation portion 23 has a cylindrical portion 23a and a pair of tapered portions 23b and 23c. When the balloon 14 is inflated, the cylindrical portion 23a is a portion of the balloon 14 whose diameter is substantially constant in the axial line direction. The tapered portion 23b extends toward the base end side from a base end of the cylindrical portion 23a. The tapered portion 23c extends toward the leading end side from a leading end of the cylindrical portion 23a. The cylindrical portion 23a is a portion over which the outer diameter of the inflation portion 23 (the balloon 14) becomes largest. The outer diameter of each of the pair of tapered portions 23b and 23c becomes gradually smaller the further from the cylindrical portion 23a.

The interior of the balloon 14 is communicated with the hub 13 via the lumen 11a of the outer shaft 11. In this way, a compressed fluid that is supplied via the hub 13 is supplied to the interior of the balloon 14 via the lumen 11a of the outer shaft 11. Thus, the lumen 11a functions as a fluid lumen to cause the compressed fluid to flow. When the compressed fluid is supplied to the interior of the balloon 14 via the lumen 11a of the outer shaft 11, the balloon 14 enters an inflated state. The inflated state is a state in which the balloon 14 has been inflated. On the other hand, when a negative pressure is applied to the lumen 11a and the compressed fluid is discharged from the interior of the balloon 14, the balloon 14 enters a deflated state. The deflated state is a state in which the balloon 14 has been deflated.

The balloon 14 is formed as a multi-wing type that has a plurality of wings in a circumferential direction. In the present embodiment, the balloon 14 is formed as a three-wing type. When the balloon 14 is in the deflated state, the inflation portion 23 is folded over so as to form the plurality of wings. Specifically, in the deflated state, the folded over plurality of wings are wound around the axis of the inner shaft 12.

The leading end portion of the inner shaft 12 extends further to the leading end side than the balloon 14. A guide wire lumen 27, through which a guide wire G can be inserted, is formed in the portion of the inner shaft 12 extending further to the leading end side than the balloon 14. The guide wire lumen 27 is formed in the leading end tip 19. Specifically, the guide wire lumen 27 is formed, in the leading end tip 19, further to the leading end side than the core wire 18. The guide wire lumen 27 is formed so as to extend in the axial line direction. A leading end opening 27a of the guide wire lumen 27 opens in a leading end surface of the leading end tip 19. A base end opening 27b of the guide wire lumen 27 opens in an outer peripheral surface 19a of the leading end tip 19. The base end opening 27b opens toward the outer side in the radial direction of the leading end tip 19. The radial direction is a direction orthogonal to the axial line direction. The outer side in the radial direction is a side separated from an axial center of the balloon catheter 10.

The guide wire G can be introduced into the guide wire lumen 27 via the leading end opening 27a, and can be drawn out to the base end side from the guide wire lumen 27 via the base end opening 27b. The guide wire G that has been drawn out from the guide wire lumen 27 is disposed along the axial line direction on the outer peripheral surface of the balloon 14, on the same side, in the circumferential direction, as the side on which the base end opening 27b opens (refer to FIG. 2B).

Two contrast rings 29 are attached to the portion of the inner shaft 12 (more specifically, of the core wire 18) that is covered by the balloon 14. One of the contrast rings 29 is attached in a position corresponding to a boundary portion between the base end side joint portion 21 and the inflation portion 23. The other contrast ring 29 is attached to a position corresponding to a boundary portion between the leading end side joint portion 22 and the inflation portion 23. The contrast rings 29 improve visibility of the position of the balloon 14 under X-ray projection, and make it easier to determine the position of the balloon 14 with respect to a targeted treatment location.

A plurality of (specifically, three) elements 31 are provided on the outer peripheral side of the balloon 14. Each of the plurality of elements 31 is formed as an elongate member made of an elastic resin material, and is specifically formed of a polyamide resin. A transverse cross section shape of the element 31 is triangular. The transverse cross section is a face that is perpendicular to the axial line direction of the element 31. Each of the elements 31 is arranged such that one edge of the triangular shape of the element 31 is positioned on the outer peripheral surface of the balloon 14, and one corner of the triangular shape protrudes outward from the outer peripheral surface of the balloon 14. Note that the transverse cross section shape of each of the elements 31 need not necessarily be triangular. The transverse cross section shape of each of the elements 31 may be circular, square, or so on. Further, the transverse cross section shape of each of the elements 31 may differ between each of the elements 31.

Each of the elements 31 is provided such that it extends across the balloon 14 in the axial line direction. A base end portion of each of the elements 31 is mounted on the outer shaft 11 via a first mounting member 32. A leading end portion of each of the elements 31 is mounted on the inner shaft 12 via a second mounting member 33. The first mounting member 32 is a cylindrical member surrounding the outer shaft 11. The first mounting member 32 is formed of a resin material. The first mounting member 32 is positioned further to the base end side than the base end side joint portion 21 of the balloon 14, and is joined to the outer shaft 11 in a position adjacent to the balloon 14. The first mounting member 32 is joined to the outer peripheral surface of the outer shaft 11 by thermal welding. Further, the base end portion of each of the elements 31 is joined to the outer peripheral surface of the first mounting member 32 by thermal welding.

Note that the first mounting member 32 may be movably provided with respect to the outer shaft 11 and need not necessarily be joined (fixed) to the outer shaft 11.

The second mounting member 33 is a cylindrical member that surrounds the inner shaft 12. The second mounting member 33 is formed of a resin material. The second mounting member 33 is positioned further to the leading end side than the leading end side joint portion 22 of the balloon 14, and is joined to the inner shaft 12 in a position adjacent to the balloon 14. Only the leading end side of the second mounting member 33 is joined to the outer peripheral surface of the inner shaft 12, and the base end side of the second mounting member 33 is separated from the outer peripheral surface of the inner shaft 12. Specifically, the second mounting member 33 is joined to the leading end tip 19. Then, the leading end portion of each of the elements 31 is joined by thermal welding to the inside surface on the base end side of the second mounting member 33. In this way, each of the plurality of elements 31 includes the base end portion joined to the outer shaft 11, and the leading end portion joined to an extending portion of the inner shaft 12 that extends further to the leading end side than the leading end side joint portion 22 of the balloon 14.

As shown in FIG. 2B, the three elements 31 are arranged at predetermined intervals along the circumferential direction of the balloon 14. The circumferential direction is a direction along the balloon 14 in the transverse cross section. Specifically, an element 31a and an element 31c are arranged at a 90 degree interval in the circumferential direction of the balloon 14. An element 31b and the element 31c are arranged at a 90 degree interval in the circumferential direction of the balloon 14. The element 31a and the element 31b are arranged at a 180 degree interval in the circumferential direction. The two elements 31a and 31b are arranged on the balloon 14 such that they are on either side of a section whose position in the circumferential direction on the balloon 14 is the same position as the base end opening 27b. Hereinafter, the section whose position in the circumferential direction on the balloon 14 is the same position as the base end opening 27b is referred to as an opening side section 39. The opening side section 39 is positioned in a central portion between the two elements 31a and 31b. Thus, of the elements 31a, 31b, and 31c arranged on the balloon 14, an interval between the two elements 31a and 31b that are positioned in the circumferential direction so as to be on either side of the opening side section 39 is larger than an interval between the two elements 31a and 31c (31b and 31c) that are adjacent to each other in the circumferential direction without being on either side of the opening side section 39.

In the opening side section 39 on the balloon 14, the guide wire G is installed so as to extend across the balloon 14 in the axial line direction. In this case, the guide wire G is installed between the two elements 31a and 31b that are adjacent to each other with the larger interval therebetween. Specifically, the guide wire G is installed in the central portion between the two elements 31a and 31b. Thus, the balloon catheter 10 is configured such that each of the elements 31a to 31c and the guide wire G are arranged at 90 degree intervals (equal intervals) in the circumferential direction on the outer peripheral surface of the balloon 14.

By arranging each of the elements 31a to 31c on the balloon 14 as described above, interference between the elements 31a to 31c and the guide wire G on the balloon 14 may be inhibited. Note that the arrangement interval and the number of the elements 31 on the balloon 14 are not necessarily limited to the examples described above, and the arrangement interval and the number may be chosen as desired.

The balloon catheter 10 is provided with an extendable/retractable portion that is extendable/retractable in the axial line direction. More specifically, the inner shaft 12 has the extendable/retractable portion. The configuration of the extendable/retractable portion will be explained below.

As shown in FIG. 2A, the inner shaft 12 has the core wire 18. The core wire 18 has a coil portion 35. The coil portion 35 is a portion of the wire 18a, which configures the wire 18, that is wound in a spiral shape (coil shape) along the axial line direction of the inner shaft 12. The coil portion 35 is extendable/retractable in the axial line direction as a result of elastic deformation. Below, a state of the extended coil portion 35 is referred to as an extended state. A state of the retracted coil portion 35 is referred to as a retracted state. FIG. 2A shows the coil portion 35 in the extended state. FIG. 3A that will be described later shows the coil portion 35 in the retracted state.

The coil portion 35 is formed by the tight winding (compact winding) of the wire 18a configuring the core wire 18. More specifically, when in a natural state in which a tensile force in the axial line direction is not imparted to the coil portion 35, the coil portion 35 is in a tightly coiled state (refer to FIG. 3A). The tightly coiled state is a state in which, in the coil portion 35, sections of the wire 18a adjacent to each other in the axial line direction are in contact (close contact) with each other.

Note that the coil portion 35 need not necessarily be in the tightly coiled state when in the natural state. The coil portion 35 may be in a roughly coiled state when in the natural state. The roughly coiled state is a state in which there are gaps between the sections of the wire 18a adjacent to each other in the axial line direction.

The coil portion 35 is arranged inside the expanded diameter portion 16 (the lumen 11a) of the outer shaft 11. Specifically, the coil portion 35 is arranged on the leading end side in the expanded diameter portion 16. More specifically, the coil portion 35 is arranged in the vicinity of the leading end portion of the expanded diameter portion 16. An outer diameter D1 (refer to FIG. 3A) of the coil portion 35 is larger than an inner diameter D2 of an area of the outer shaft 11 further to the leading end side than the expanded diameter portion 16 (D1>D2). Further, the outer diameter D1 (coil diameter) of the coil portion 35 is smaller than an inner diameter D3 of the expanded diameter portion 16 (D1<D3). Thus, when the coil portion 35 is arranged inside the expanded diameter portion 16, a predetermined gap 37 is formed between the outer peripheral surface of the coil portion 35 and the inner peripheral surface of the expanded diameter portion 16. In a section of the expanded diameter portion 16 in which the coil portion 35 is arranged, the fluid flows through the gap 37 and the inside of the coil portion 35.

An operation of the coil portion 35 will be explained with reference to FIG. 3. FIG. 3A and FIG. 3B are vertical cross sections illustrating the operation of the coil portion 35. FIG. 3A shows the deflated state of the balloon 14. FIG. 3B shows the inflated state of the balloon 14.

As shown in FIG. 3A, when the balloon 14 is in the deflated state, the coil portion 35 is in the natural state, namely, is in the retracted state (contracted state). In this case, a length of the balloon 14 in the axial line direction is a length L1, and a length of the coil portion 35 in the axial line direction is a length L2.

As shown in FIG. 3B, when the compressed fluid is introduced into the balloon 14, the balloon 14 enters into the inflated state. When the balloon 14 inflates, in addition to expanding in the radial direction, the balloon 14 expands (extends) in the axial line direction. In this case, the balloon 14 extends in the axial line direction by $\Delta L$, and the length in the axial line direction becomes L3 (L3−L1=$\Delta L$).

Specifically, when the balloon 14 inflates, the balloon 14 extends by $\Delta L$ toward the leading end side with respect to the outer shaft 11 in the axial line direction. Then, in accordance with the extension of the balloon 14, the inner shaft 12 (the core wire 18) that is joined to the leading end portion of the balloon 14 is pulled to the leading end side by the balloon 14. When the inner shaft 12 is pulled to the leading end side, the coil portion 35 of the core wire 18 extends in the axial line direction. Specifically, the coil portion 35 extends by the same length as the extension amount $\Delta L$ of the balloon 14 in the axial line direction. As a result, the length of the coil portion 35 in the axial line direction becomes a length L4 (L4−L2=$\Delta L$). In other words, in this case, when the coil portion 35 extends in the axial line direction, the inner shaft 12 is displaced toward the leading end side by the extension amount $\Delta L$ of the balloon 14 in the axial line direction. In this way, the occurrence of warping of the balloon 14 may be suppressed.

After that, when the compressed fluid is discharged from the balloon 14, the balloon 14 enters into the deflated state. When the balloon 14 is in the deflated state, the tensile force that was acting on the coil portion 35 in the axial line direction due to the balloon 14 is no longer present. The coil portion 35 contracts in the axial line direction due to its own elasticity (return elasticity). As a result, the coil portion 35 returns to the natural state and the length thereof in the axial line direction returns to the original length L2. In other words, the length of the coil portion 35 returns to the length L2 before the balloon inflation. Further, since the length of the coil portion 35 returns to the original length L2, the length of the balloon 14 in the axial line direction also returns to the original length L1. Thus, in this case, the balloon 14 returns to the original (pre-inflation) deflated state (the state shown in FIG. 3A).

Next, a method of use of the balloon catheter 10 will be briefly explained.

A user inserts a guiding catheter through a sheath introducer that has first been inserted into a blood vessel, and introduces a leading end opening portion of the guiding catheter as far as a coronary artery entry portion. Next, the user inserts the guide wire G through the guiding catheter and introduces the inserted guide wire G from the coronary artery entry portion as far as a peripheral portion via a portion to be treated, such as a constricted portion.

Next, the user introduces the balloon catheter 10 into the guiding catheter along with the guide wire G. When introducing the balloon catheter 10, of the outer shaft 11, only a section further to the leading end side than the expanded diameter portion 16 is introduced into the guiding catheter, and the expanded diameter portion 16 is thus not introduced into the guiding catheter (namely, is not introduced into the body). After the balloon catheter 10 has been introduced into the guiding catheter, the balloon 14 is arranged at the portion to be treated while applying a push and pull maneuver.

Next, the user supplies the compressed fluid to the balloon 14 via the lumen 11a of the outer shaft 11, from the hub 13 side, using a pressurizer. In this way, the balloon 14 is inflated. When the balloon 14 inflates, the constricted portion is expanded. Further, in accordance with the inflation of the balloon 14, the respective elements 31 arranged on the outer peripheral side of the balloon 14 are pressed against the blood vessel wall by the balloon 14, and bite into the blood vessel wall. In this way, the balloon 14 may be inhibited from slipping from the constricted portion.

As described above, when the balloon 14 is inflated, the occurrence of warping of the balloon 14 is suppressed by the operation of the coil portion 35. It is thus possible to avoid occurrence of a situation in which the respective elements 31 are not arranged at the predetermined intervals around the balloon 14, such as becoming concentrated, on the outer peripheral side of the balloon 14, on the opposite side to a side on which the balloon 14 is warping. As a result, each of the elements 31 may favorably function in being able to stop the slipping of the balloon 14.

After the user finishes expanding the constricted portion using the balloon 14, the user discharges the compressed fluid from the balloon 14 and causes the balloon 14 to be in the deflated state. Then, the user pulls out the balloon 14 in the deflated state, namely, the balloon catheter 10, from the body. Since the balloon 14 returns to the original (pre-inflation) deflated state by being once more deflated, as described above, in this case, it is possible to suppress a deterioration in operability when pulling out the balloon 14.

According to the configuration of the present embodiment described in detail above, the following effects may be obtained.

The coil portion 35 is formed by winding the wire 18a, which configures the core wire 18, in the spiral shape in the axial line direction. Then, the extendable/retractable portion is configured that is extendable/retractable in the axial line direction by the coil portion 35. In this case, in comparison to a case in which the extendable/retractable portion is formed of a highly pliable material (such as a rubber material), the extendable/retractable portion may be formed while inhibiting a significant deterioration in rigidity.

A dimension in the radial direction of the coil portion 35 is larger than that of other portions of the coil wire 18. Thus, when the coil portion 35 is arranged inside the balloon 14, a balloon diameter increases at the time of the deflation of the balloon 14, and there is a risk that passability of the balloon 14 inside the body may deteriorate. With respect to this point, the coil portion 35 is arranged further to the base end side than the balloon 14, and thus, the warping of the balloon 14 may be suppressed while inhibiting the deterioration in the passability of the balloon 14.

A portion on the base end side of the outer shaft 11 has the expanded diameter portion 16 that has an expanded diameter compared to the leading end side thereof. The coil portion 35 is arranged inside the expanded diameter portion 16. In this case, the coil portion 35 whose dimension in the radial direction is large may be arranged inside the outer shaft 11. Further, since the expanded diameter portion 16 is provided on the base end side of the outer shaft 11, it is possible not to introduce the expanded diameter portion 16 into the body when the outer shaft 11 is introduced into the body. In this way, the coil portion 35 may be arranged inside the outer shaft 11 while inhibiting a deterioration in the insertability of the outer shaft 11.

The coil portion 35 is positioned on the leading end side in the expanded diameter portion 16. Thus, a configuration is obtained in which the coil portion 35 is arranged in the expanded diameter portion 16, and a length of the portion of the core wire 18 further to the leading end side than the coil portion 35 may be made shorter. In this way, when the above-described leading end side portion is displaced in the axial line direction in accordance with the extension and retraction of the coil portion 35, it is possible to reduce resistance when the leading end side portion slides along the inner peripheral surface of the outer shaft 11. As a result, even with this configuration, the extension and retraction functions of the coil portion 35 may be favorably exhibited.

The present disclosure is not limited to the above-described embodiment, and may be performed in the following manner, for example.

Figure 4A:
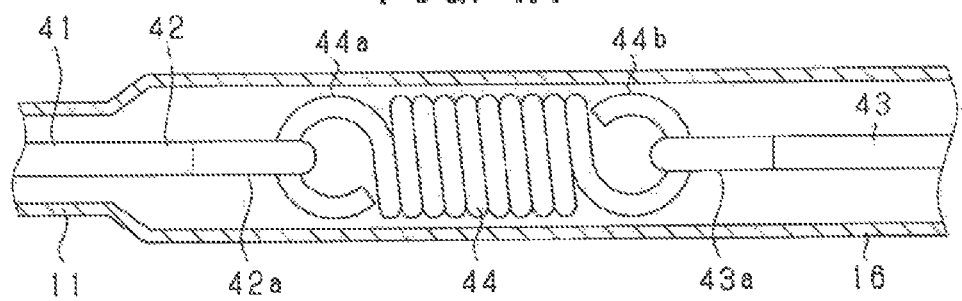
FIG. 4A and FIG. 4B are a front view showing another embodiment of an extendable/retractable portion.

(1) In the above-described embodiment, a part of the core wire 18 is used to form the coil portion 35. However, the coil portion may formed separately from a core wire. For example, as shown in an example in FIG. 4A, a core wire 41 has a plurality of wire portions 42 and 43 that are divided partway along the axial line direction. In the example shown in FIG. 4A, the core wire 41 has two wire portions 42 and 43. A coil spring 44, which is formed separately from the core wire 41 (the wire portions 42 and 43), is provided between the two wire portions 42 and 43. One end of the coil spring 44 is attached to a base end of the wire portion 42. The other end of the coil spring 44 is attached to a leading end of the wire portion 43.

The coil spring 44 is formed by winding a metal (stainless steel, for example) wire in a spiral shape in the axial line direction of a catheter. Hook portions 44a and 44b are respectively provided on both end portions of the coil spring 44. Meanwhile, hook portions 42a and 43a are respectively provided on end portions, of each of the wire portions 42 and 43, on the coil spring 44 side. The hook portion 42a of the wire portion 42 is hooked onto the hook portion 44a of the coil spring 44, and the hook portion 43a of the wire portion 43 is hooked onto the hook portion 44b of the coil spring 44. In this way, the coil spring 44 is attached to each of the wire portions 42 and 43, respectively.

According to this configuration, since the coil spring 44 is formed separately from the core wire 41, freedom of design of the coil portion may be enhanced. Thus, the coil portion may be favorably designed in accordance with the specifications (the size and shape, inflation pressure and the like) of the balloon 14. Note that, in this case, an inner shaft is configured including the coil spring 44 and the core wire 41.

Figure 4B:
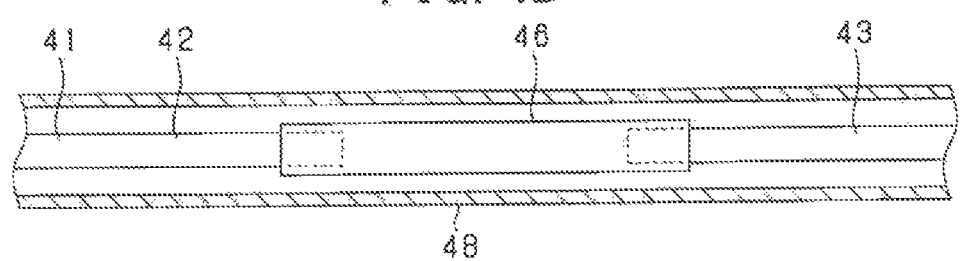

(2) In the above-described embodiment, the coil portion 35 is provided as the extendable/retractable portion that is configured to extend and retract in the axial line direction as a result of elastic deformation. However, the extendable/retractable portion need not necessarily be the coil portion 35. For example, as shown in FIG. 4B, a resin tube 46 formed of an elastic resin material (a rubber material, for example) may be used as the extendable/retractable portion. The resin tube 46 is configured to be extendable and retractable in the axial line direction as a result of elastic deformation. In the example shown in FIG. 4B, similarly to the above-described example shown in FIG. 4A, the core wire 41 has the plurality of wire portions 42 and 43 divided in the axial line direction, and the resin tube 46 is provided between the wire portions 42 and 43. The base end portion of the wire portion 42 is inserted into the leading end side of the resin tube 46. In a state in which the wire portion 42 is inserted into the resin tube 46, the resin tube 46 and the wire portion 42 are joined together by bonding. Further, the leading end portion of the wire portion 43 is inserted into the base end side of the resin tube 46. In a state in which the wire portion 43 is inserted into the resin tube 46, the resin tube 46 and the wire portion 43 are joined together by bonding. In other words, in this case, the two wire portions 42 and 43 are connected via the resin tube 46.

With this configuration also, the resin tube 46 is configured to extend and retract in the axial line direction as a result of elastic deformation, and thus, the resin tube 46 is used as the extendable/retractable portion. Further, the resin tube 46 differs from the coil portion 35 and the coil spring 44 in that the dimension thereof in the radial direction does not become particularly large. In this case, the coil portion (the resin tube 46) may be arranged inside the outer shaft 11 without providing the expanded diameter portion 16 on the outer shaft 11. It should be noted that, in this case, an inner shaft is configured so as to include the core wire 41 and the resin tube 46.

(3) In the above-described embodiment, the coil portion 35 is provided as the extendable/retractable portion that is configured to extend and retract as a result of elastic deformation. However, the extendable/retractable portion need not necessarily be extendable and retractable as a result of elastic deformation. For example, a waveform portion may be used as the extendable/retractable portion. The waveform portion is a portion in which a part of a core wire (a wire) is formed in a wave shape (zigzag shape) along the axial line direction. The waveform portion is configured such that it is foldable and expandable in the axial line direction as a result of an external force being applied in the axial line direction. When the waveform portion is folded, it becomes shorter in the axial line direction, and when it expands, it becomes longer in the axial line direction. In other words, the waveform portion is extendable and retractable in the axial line direction. Thus, the waveform portion may be used as the extendable/retractable portion.

(4) The core wire 18 may have an extension portion that is configured to only extend in the axial line direction, in place of the coil portion 35 (the extendable/retractable portion) that is extendable and retractable in the axial line direction. The extension portion is formed of a plastically deformable material, for example, and extends in the axial line direction as a result of plastic deformation when a tensile force is applied in the axial line direction. Further, when the extension portion is once caused to be in an extended state, the extended state is continuously maintained. With this configuration also, when the balloon 14 extends in the axial line direction, the inner shaft 12 is pulled further to the leading end side than the balloon 14, and the extension portion extends in the axial line direction. In other words, in this case also, since the joint portion between the inner shaft 12 and the balloon 14 is displaced to the leading end side by the extension portion extending, the occurrence of warping of the balloon 14 may be suppressed.

(5) In the above-described embodiment, the coil portion 35 is arranged on the leading end side in the expanded diameter portion 16 of the outer shaft 11. However, the coil portion 35 may be arranged on the base end side in the expanded diameter portion 16. Further, the coil portion 35 may be arranged further to the leading end side than the expanded diameter portion 16, in the outer shaft 11. In this case, it is sufficient that the outer diameter of the coil portion 35 be smaller than the inner diameter of the outer shaft 11 at a portion further to the leading end side than the expanded diameter portion 16. Further, the coil portion 35 may be provided inside the balloon 14. In this case, the size of the coil portion 35 may be set while taking into consideration the outer diameter of the balloon 14 when the balloon 14 is deflated. Even in this case, the coil portion 35 is positioned further to the base end side than the leading end side joint portion 22 of the balloon 14. Thus, by the inner shaft 12 being pulled to the leading end side in accordance with the inflation of the balloon 14, the coil portion 35 extends in the axial line direction. The warping of the balloon 14 is suppressed by the coil portion 35 extending.

(6) In the above-described embodiment, the core wire 18 has the single coil portion 35. However, the core wire 18 may have a plurality of the coil portions 35 arranged at predetermined intervals in the axial line direction.

(7) In the above-described embodiment, the solid core wire 18 is used as a part of the inner shaft 12. However, a hollow tube may be used in place of the core wire 18. Then, a coil portion may be formed using the hollow tube.

(8) In the above-described embodiment, the elements 31 are provided on the outer peripheral side of the balloon 14. However, the elements 31 need not necessarily be provided on the outer peripheral side of the balloon 14. Specifically, the balloon catheter 10 need not necessarily be provided with the elements 31. Further, in the above-described embodiment, the plurality of elements 31 are provided. However, a number of the elements 31 may be one.

(9) In the above-described embodiment, the balloon catheter 10 used for the treatment of a coronary artery is exemplified. However, the technical features disclosed in the above-described embodiment may be applied to a balloon catheter used in other blood vessels, such as a femoral artery or a pulmonary artery, or alternatively, in a urinary tract or gastrointestinal tract or other in vivo "tubes" and "cavities."

(10) In the above-described embodiment, the inner shaft 12 has the core wire 18 and the leading end tip 19. However, the inner shaft 12 need not necessarily be provided with the leading end tip 19. For example, the inner shaft 12 may be configured by a single core wire. In this case, it is sufficient that the core wire be a hollow member, for example, and be a member in which a guide wire lumen 27 is formed in a portion that protrudes further to the leading end side than the leading end of the balloon 14. In this case, the core wire may include a configuration corresponding to the extension portion, such as the coil portion 35, the resin tube 46 or the like.

(11) In the above-described embodiment, the base end opening 27b that is a guide wire opening is positioned further to the leading end side than the leading end of the balloon 14. However, the guide wire opening may be positioned further to the base end side than the base end of the balloon 14. In this case, for example, the inner shaft 12 may be provided with the core wire 18, a hollow tube, and the leading end tip 19 in that order from the base end side. In this case, it is sufficient that the leading end of the core wire 18 be positioned further to the base end side than the base end of the balloon 14, and that the hollow tube be joined to the leading end side of the core wire 18. Then, the guide wire opening may be formed in the hollow tube in a position partway along the axial line direction.

(12) In the above-described embodiment, the base end portion of the leading end tip 19 is in substantially the same position as the base end portion of the leading end side joint portion 22 of the balloon 14. However, the base end portion of the leading end tip 19 may be in a different position to the base end portion of the leading end side joint portion 22. For example, the base end portion of the leading end tip 19 may be positioned further to the base end side than the base end side joint portion 21 of the balloon 14. In this case, it is sufficient that the leading end tip 19 be a hollow member that extends inside the balloon 14. Further, in this case, it is sufficient that the guide wire lumen 27 be configured such that openings respectively formed in the outer peripheral surface of the outer shaft 11 and in the outer peripheral surface of the leading end tip 19 communicate with each other.

(13) In the above-described embodiment, the outer shaft 11 includes the expanded diameter portion 16. However, the outer shaft 11 need not necessarily include the expanded diameter portion 16. In this case, for example, the outer shaft 11 may be a cylindrical member whose inner diameter and outer diameter are substantially constant in the axial line direction. Further, the outer shaft 11 may be configured such that the inner diameter is substantially constant in the axial line direction while the outer diameter changes in the axial line direction. Further, the outer shaft 11 may be a tubular member whose outer diameter changes at a predetermined position in the axial line direction.

(14) In the above-described embodiment, the plurality of elements 31 are joined to the outer shaft 11 and the inner shaft 12 via the first mounting member 32 and the second mounting member 33. However, the balloon catheter 10 need not necessarily be provided with the first mounting member 32 and the second mounting member 33. For example, the plurality of elements 31 may be directly joined to the outer shaft 11 and the inner shaft 12. Further, the balloon catheter 10 may be provided with only one of the first mounting member 32 and the second mounting member 33.

(15) In the above-described embodiment, the leading end portions of the plurality of elements 31 are joined to the leading end tip 19. However, the leading end portions of the plurality of elements 31 may be joined to the core wire 18.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A balloon catheter comprising:
an outer shaft having a leading end and a base end;
an inner shaft inserted inside the outer shaft, a part of the inner shaft extending beyond the leading end of the outer shaft; and
an inflatable balloon having a base end side joint portion and a leading end side joint portion, wherein the base end side joint portion of the inflatable balloon is joined to the outer shaft and wherein the leading end side joint portion of the inflatable balloon is joined to the inner shaft,
wherein the inner shaft has an extension portion configured to extend in an axial line direction, the extension portion including a leading end and a base end,
wherein a distance between the leading end of the extension portion and the base end side joint portion of the inflatable balloon is a first distance,
wherein a distance between the leading end of the extension portion and the leading end side joint portion of the inflatable balloon is a second distance,
wherein the first distance is less than the second distance,
wherein all of the extension portion is located closer to the base end side joint portion of the inflatable balloon than the leading end side joint portion of the inflatable balloon,
wherein the leading end of the outer shaft has a first inner diameter,
wherein the base end of the outer shaft includes an expanded diameter portion, the expanded diameter portion having an expanded inner diameter,
wherein the expanded inner diameter of the expanded diameter portion is greater than the first inner diameter,
wherein the extension portion is arranged inside the expanded diameter portion,
wherein the extension portion is an extendable/retractable portion configured to extend and retract in the axial line direction as a result of elastic deformation,
wherein the extension portion, when extended, has a first outer diameter that is greater than the first inner diameter,
wherein the extension portion, when retracted, has a second outer diameter that is greater than the first inner diameter,
wherein the expanded inner diameter of the expanded diameter portion is greater than the first outer diameter and the second outer diameter,
wherein the base end side joint portion of the inflatable balloon is positioned between a leading end of the expanded diameter portion and the leading end side joint portion of the inflatable balloon,
wherein the extension portion, when extended, does not contact the expanded diameter portion, and
wherein the extension portion, when retracted, does not contact the expanded diameter portion.

2. The balloon catheter according to claim 1,
wherein the expanded diameter portion includes a base end, and
wherein the extension portion is arranged at the leading end of the expanded diameter portion of the outer shaft and extends toward the base end of the expanded diameter portion.

3. The balloon catheter according to claim 1,
wherein the inner shaft further comprises a leading end portion,
wherein the balloon catheter further comprises:
a plurality of elongate members, each of the elongate members being provided on an outer peripheral side of the inflatable balloon and extending along the inflatable balloon in the axial line direction, and being arranged at predetermined intervals in a circumferential direction of the inflatable balloon,
wherein each of the plurality of elongate members includes
a base end portion joined to the outer shaft, and
a leading end portion joined to the leading end portion of the inner shaft, and
wherein the leading end portion of the inner shaft extends beyond the leading end side joint portion of the inflatable balloon.

4. The balloon catheter according to claim 3,
wherein the inner shaft further comprises a tip located at the leading end portion of the inner shaft, the tip comprising a leading end portion and a base end portion, the base end portion of the tip having an opening in a radial direction of the base end portion,
wherein the tip includes a guide wire lumen, the guide wire lumen extending from the leading end portion of the tip to the opening, wherein the inflatable balloon includes an outer peripheral surface having a circumference along a circumferential direction,
wherein the plurality of elongate members divide the circumference of the outer peripheral surface of the inflatable balloon into a plurality of sections,
wherein a first of the plurality of sections is aligned with the opening of the base end portion of the guide wire lumen,
wherein a second of the plurality of the sections is not aligned with the opening of the base end portion of the guide wire lumen, and
wherein the first of the plurality of sections has a greater dimension in the circumferential direction of the inflatable balloon than a dimension in the circumferential direction of the second of the plurality of sections.

5. The balloon catheter according to claim 1,
wherein the expanded inner diameter when the extension portion is extended is the same as the expanded inner diameter when the extension portion is retracted.

6. A balloon catheter comprising:
an outer shaft having a leading end and a base end;
an inner shaft inserted inside the outer shaft, a part of the inner shaft extending beyond the leading end of the outer shaft; and
an inflatable balloon having a base end side joint portion and a leading end side joint portion, wherein the base end side joint portion of the inflatable balloon is joined, at a first location, to the outer shaft and wherein the leading end side joint portion of the inflatable balloon is joined, at a second location, to the inner shaft,
wherein the inner shaft has an extension portion, at a third location, configured to extend in an axial line direction, the extension portion including a leading end and a base end,
wherein the first location is between the second location and the third location,
wherein the leading end of the outer shaft has a first inner diameter,
wherein the base end of the outer shaft includes an expanded diameter portion, the expanded diameter portion including a first portion and a second portion, an inner diameter of the first portion being an expanded inner diameter, an inner diameter of the second portion increasing from the first inner diameter to the expanded inner diameter,
wherein the second portion is located at a fourth location,
wherein the expanded inner diameter of the expanded diameter portion is greater than the first inner diameter,
wherein the extension portion is arranged inside the expanded diameter portion,
wherein the extension portion is an extendable/retractable portion configured to extend and retract in the axial line direction as a result of elastic deformation,
wherein the extension portion, when extended, has a first outer diameter that is greater than the first inner diameter,
wherein the extension portion, when retracted, has a second outer diameter that is greater than the first inner diameter,
wherein the first location is between the second location and the fourth location,
wherein the extendable/retractable portion is a coil portion formed of a wound wire, wound in a spiral shape in the axial line direction, and
wherein at least a part of the inner shaft is the extendable/retractable portion.

7. The balloon catheter according to claim 6,
wherein the expanded diameter portion includes a leading end and a base end, and
wherein the extension portion is arranged at the leading end of the expanded diameter portion of the outer shaft and extends toward the base end of the expanded diameter portion.

8. The balloon catheter according to claim 6,
wherein the inner shaft further comprises a leading end portion,
wherein the balloon catheter further comprises:
a plurality of elongate members, each of the elongate members being provided on an outer peripheral side of the inflatable balloon and extending along the inflatable balloon in the axial line direction, and being arranged at predetermined intervals in a circumferential direction of the inflatable balloon,
wherein each of the plurality of elongate members includes
a base end portion joined to the outer shaft, and
a leading end portion joined to the leading end portion of the inner shaft, and
wherein the leading end portion of the inner shaft extends beyond the leading end side joint portion of the inflatable balloon.

9. The balloon catheter according to claim 8,
wherein the inner shaft further comprises a tip located at the leading end portion of the inner shaft, the tip comprising a leading end portion and a base end portion, the base end portion of the tip having an opening in a radial direction of the base end portion, and
wherein the tip includes a guide wire lumen, the guide wire lumen extending from the leading end portion of the tip to the opening.

10. The balloon catheter according to claim 9,
wherein the inflatable balloon includes an outer peripheral surface having a circumference along a circumferential direction,
wherein the plurality of elongate members divide the circumference of the outer peripheral surface of the inflatable balloon into a plurality of sections,
wherein a first of the plurality of sections is aligned with the opening of the base end portion of the guide wire lumen,
wherein a second of the plurality of the sections is not aligned with the opening of the base end portion of the guide wire lumen, and
wherein the first of the plurality of sections has a greater dimension in the circumferential direction of the inflatable balloon than a dimension in the circumferential direction of the second of the plurality of sections.

11. The balloon catheter according to claim 6,
wherein the expanded inner diameter when the extension portion is extended is the same as the expanded inner diameter when the extension portion is retracted.

12. A balloon catheter comprising:
an outer shaft having a leading end and a base end;
an inner shaft inserted inside the outer shaft, a part of the inner shaft extending beyond the leading end of the outer shaft; and
an inflatable balloon having a base end side joint portion and a leading end side joint portion, wherein the base end side joint portion of the inflatable balloon is joined, at a first location, to the outer shaft and wherein the leading end side joint portion of the inflatable balloon is joined, at a second location, to the inner shaft, wherein the inner shaft has an extension portion, at a third location, configured to extend in an axial line direction, the extension portion including a leading end and a base end, wherein the first location is between the second location and the third location, wherein the leading end of the outer shaft has a first inner diameter, wherein the base end of the outer shaft includes an expanded diameter portion, the expanded diameter portion having an expanded inner diameter, wherein a portion of the expanded diameter portion that is closest to the second location is located at a fourth location, wherein the expanded inner diameter of the expanded diameter portion is greater than the first inner diameter, wherein the extension portion is arranged inside the expanded diameter portion, wherein the extension portion is an extendable/retractable portion configured to extend and retract in the axial line direction as a result of elastic deformation, wherein the extension portion, when extended, has a first outer diameter that is greater than the first inner diameter, wherein the extension portion, when retracted, has a second outer diameter that is greater than the first inner diameter, wherein the first location is between the second location and the fourth location, wherein the extension portion, when extended, does not contact the expanded diameter portion, and wherein the extension portion, when retracted, does not contact the expanded diameter portion.

13. The balloon catheter according to claim 12, wherein the expanded inner diameter when the extension portion is extended is the same as the expanded inner diameter when the extension portion is retracted.

* * * * *